United States Patent [19]

Gesing et al.

[11] Patent Number: 5,677,307

[45] Date of Patent: Oct. 14, 1997

[54] SUBSTITUTED TETRAHYDRO-5-NITRO-PYRIMIDINES

[75] Inventors: Ernst Rudolf Gesing, Erkrath; Hilmar Wolf, Langenfeld; Christoph Erdelen, Leichlingen; Ulrike Wachendorff-Neumann, Neuwied; Wolfram Andersch, Bergisch Gladbach; Andreas Turberg, Erkrath; Norbert Mencke, Leverkusen, all of Germany

[73] Assignee: Bayer Aktiengesellschaft, Leverkusen, Germany

[21] Appl. No.: 691,834

[22] Filed: Aug. 2, 1996

[30] Foreign Application Priority Data

Aug. 10, 1995 [DE] Germany .................. 195 29 411.4

[51] Int. Cl.[6] .................. A61K 31/505; C01D 521/00
[52] U.S. Cl. .................. 514/258; 544/279; 544/281
[58] Field of Search .................. 544/279, 281; 514/258

[56] References Cited

U.S. PATENT DOCUMENTS 4,831,036  5/1989  Wolf et al. .................. 514/258

FOREIGN PATENT DOCUMENTS

| 0 247 477 A1 | 12/1987 | European Pat. Off. ...... C07D 487/04 |
| 0 316 843 A2 | 5/1989 | European Pat. Off. ...... C07D 487/04 |
| 0 316 845 A2 | 5/1989 | European Pat. Off. ...... C07D 487/04 |
| WO94/05670 | 3/1994 | WIPO .................. C07D 487/04 |

Primary Examiner—Robert T. Bond
Attorney, Agent, or Firm—Sprung Kramer Schaefer & Briscoe

[57] ABSTRACT

The present invention relates to novel substituted in that one tetrahydro-5-nitro-pyrimidine of the formula (I), according to claim 1,

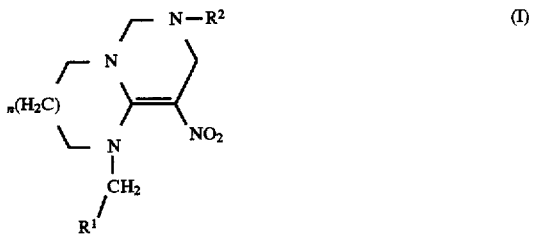

in which n, $R^1$, $R^2$ have the meaning given in the description, to a process for its preparation and to its use for combating animal pests, especially insects, arachnids and nematodes, which are encountered in agricultural, in forestry, in the protection of stored products and of materials and, in the hygiene sector.

8 Claims, No Drawings

SUBSTITUTED TETRAHYDRO-5-NITRO-PYRIMIDINES

The present invention relates to novel tetrahydro-5-nitro-pyrimidines, to a process for their preparation and to their use for combating animal pests, especially insects, arachnids and nematodes, which are encountered in agriculture, in forestry, in the protection of stored products and of materials, and in the hygiene sector.

It is already known that certain 1,2,3,6-tetrahydro-5-nitro-pyrimidine derivatives have insecticidal properties (cf. DE-A 36 38 121, EP-A 0 316 843 and EP-A 0 316 845). The action of these compounds, however, is not always satisfactory, especially at low application rates and low concentrations.

Novel substituted tetrahydro-5-nitro-pyrimidines have now been found of the formula (I)

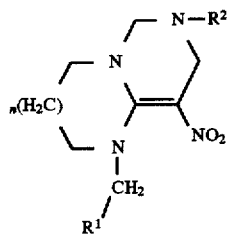

in which n represents 0 or 1, $R^1$ represents optionally substituted pyridyl or optionally substituted thiazolyl and $R^2$ represents one of the following groups:

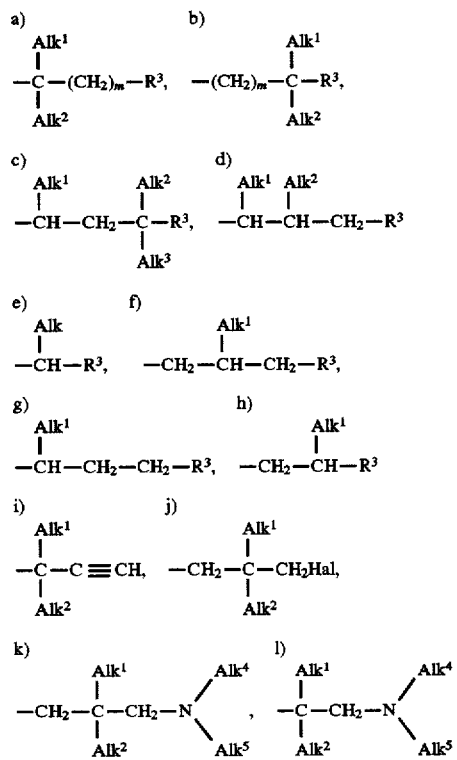

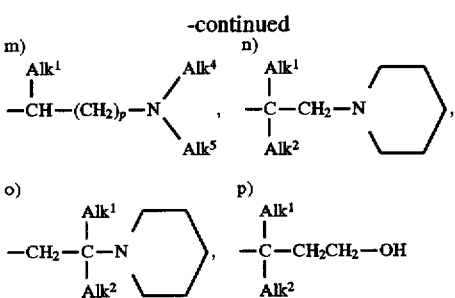

in which

Alk represents alkyl having more than 1 carbon atom, $Alk^1$ to $Alk^6$ independently of one another represent alkyl, Hal represents halogen, m represents 1 or 2, p represents 1, 2 or 3, r and s independently of one another represent 0, 1, 2, 3 or 4, $R^3$ represents in each case optionally substituted phenyl, pyridyl or N-morpholino, $R^4$ represents in each case optionally substituted phenyl or thienyl, $R^5$ represents in each case optionally substituted phenyl, naphthyl or pyridyl and X represents oxygen, sulphur or the group $NAlk^7$, in which $Alk^7$ represents alkyl.

It has additionally been found that the substituted tetrahydro-5-nitro-pyrimidines of the formula (I) are obtained if nitromethylene derivatives of the formula (II)

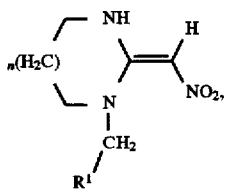

in which $R^1$ and n have the meaning given above are reacted with amines of the formula (III)

$$H_2N-R^2 \quad (III),$$

in which $R^2$ has the meaning given above in the presence of at least twice the molar quantity of formaldehyde, optionally in the presence of an acidic catalyst and optionally in the presence of a diluent.

The substituted tetrahydro-5-nitro-pyrimidines of the formula (I) possess optionally asymmetrically substituted carbon atoms and can therefore occur in different optical isomers. The present invention relates to both the isomer mixtures and the pure isomers.

Finally, it has been found that the novel substituted tetrahydro-5-nitro-pyrimidines of the formula (I) possess very pronounced biological properties and are suitable in particular for combating animal pests, especially insects, arachnids and nematodes, which are encountered in agriculture, in forestry, in the protection of stored products and of materials and in the hygiene sector.

A general definition of the substituted tetrahydro-5-nitro-pyrimidines according to the invention is given by the formula (I).

Preferred substituents and ranges of the radicals shown in the above-mentioned and below-mentioned formulae are detailed as follows:

n preferably represents 0 or 1.

$R^1$ preferably represents pyridyl which is optionally substituted from one to three times by identical or different substituents or represents thiazolyl which is optionally substituted from one to two times by identical or different substituents, possible substituents in each case being:

halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy and $C_1$–$C_4$-halogenoalkylthio.

$R^2$ preferably represents the groups (a) to (y).

Alk preferably represents $C_2$–$C_4$-alkyl.

$Alk^1$ to $Alk^6$ independently of one another preferably represent $C_1$–$C_4$-alkyl.

Hal preferably represents fluorine, chlorine or bromine.

m preferably represents 1 or 2.

p preferably represents 1, 2 or 3.

r and s independently of one another preferably represent 0, 1, 2, 3 or 4.

$R^3$ preferably represents phenyl which is optionally substituted from one to five times by identical or different substituents or represents pyridyl which is optionally substituted from one to four times by identical or different substituents, possible substituents in each case being:

halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, amino, $C_1$–$C_4$-alkylamino and di($C_1$–$C_4$-alkyl)amino;

and represents N-morpholino which is optionally substituted from one to two times by identical or different substituents, suitable substituents being: halogen, $C_1$–$C_4$-alkyl, $C_1$–$C_4$-alkoxy and $C_1$–$C_4$-halogenoalkyl.

$R^4$ preferably represents phenyl which is optionally substituted from one to five times by identical or different substituents or represents thienyl which is optionally substituted from one to three times by identical or different substituents, possible substituents in each case being:

halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, amino, $C_1$–$C_4$-alkylamino and di($C_1$–$C_4$-alkyl)amino.

$R^5$ preferably represents phenyl which is optionally substituted from one to five times by identical or different substituents, naphthyl which is optionally substituted from one to three times by identical or different substituents or represents pyridyl which is optionally substituted from one to four times by identical or different substituents, possible substituents in each case being:

halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, amino, $C_1$–$C_4$-alkylamino and di($C_1$–$C_4$-alkyl)amino.

X preferably represents oxygen, sulphur or the group $NAlk^7$ in which $Alk^7$ represents $C_1$–$C_4$-alkyl.

n particularly preferably represents 0 or 1.

$R^1$ particularly preferably represents pyridyl which is optionally substituted from one to two times by identical or different substituents or represents thiazolyl which is optionally substituted once, possible substituents in each case being:

fluorine, chlorine, bromine, cyano, nitro, methyl, ethyl, methoxy, methylthio, trifluoromethyl, trifluoromethoxy and trifluoromethylthio.

$R^2$ particularly preferably represents the groups (a) to (y).

Alk particularly preferably represents ethyl, n-propyl and isopropyl.

$Alk^1$ to $Alk^6$ independently of one another particularly preferably represent methyl, ethyl and n-propyl or isopropyl.

Hal particularly preferably represents fluorine and chlorine.

m particularly preferably represents 1 or 2.

p particularly preferably represents 1, 2 or 3.

r and s independently of one another particularly preferably represent 0, 1, 2, 3 or 4.

$R^3$ particularly preferably represents phenyl which is optionally substituted from one to three times by identical or different substituents or represents pyridyl which is optionally substituted from one to two times by identical or different substituents, possible substituents in each case being:

fluorine, chlorine, bromine, cyano, nitro, methyl, ethyl, n-propyl or isopropyl, t-butyl, trifluoromethyl, methoxy, ethoxy, trifluoromethoxy, trifluoromethylthio, dimethylamino, methylethylamino and diethylamino;

and represents N-morpholino which is optionally substituted from one to two times by identical or different substituents, possible substituents being: methyl, ethyl, methoxy and trifluoromethyl.

$R^4$ particularly preferably represents phenyl which is optionally substituted from one to three times by identical or different substituents or represents thienyl which is optionally substituted from one to two times by identical or different substituents, possible substituents in each case being:

fluorine, chlorine, bromine, cyano, nitro, methyl, ethyl, n-propyl or isopropyl, t-butyl, trifluoromethyl, methoxy, ethoxy, trifluoromethoxy, trifluoromethylthio, dimethylamino, methylethylamino and diethylamino;

$R^5$ particularly preferably represents phenyl and naphthyl which are in each case optionally substituted from one to three times by identical or different substituents, or represents pyridyl which is optionally substituted from one to two times by identical or different substituents, possible substituents in each case being:

fluorine, chlorine, bromine, cyano, nitro, methyl, ethyl, n-propyl or isopropyl, t-butyl, trifluoromethyl, methoxy, ethoxy, trifluoromethoxy, trifluoromethylthio, dimethylamino, methylethylamino and diethylamino.

X particularly preferably represents oxygen, sulphur, N-methyl, N-ethyl, N-n-propyl and N-isopropyl.

The definitions and explanations of radicals given above in general or given in ranges of preference apply to the end products and, correspondingly, to the starting materials and intermediates. These definitions of radicals can be combined as desired with one another, thus including combinations between the respective ranges of preference.

Preference is given, in accordance with the invention, to the compounds of the general formula (I) in which there is a combination of the definitions given above as preferred (preferably).

Particular preference is given, in accordance with the invention, to the compounds of the general formula (I) in which there is a combination of the definitions given above as particularly preferred.

In the definitions of radicals given above and below, hydrocarbon radicals such as alkyl or alkenyl—alone or in joined forms with heteroatoms, such as alkoxy or alylthio—are, where possible, in each case straight-chain or branched.

Preferred compounds according to the invention are substances of the formulae (Ia) to (Id):

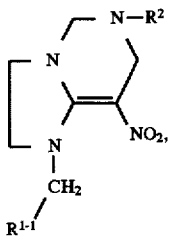
(Ia)

in which
R$^{1-1}$ represents optionally substituted pyridyl and
R$^2$ has the meanings given in the definition of the invention.

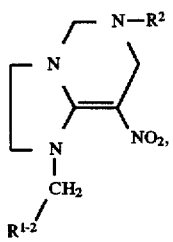
(Ib)

in which
R$^{1-2}$ represents optionally substituted thiazolyl and
R$^2$ has the meanings given in the definition of the invention.

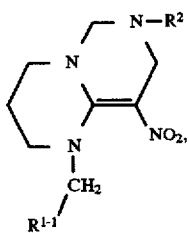
(Ic)

in which
R$^{1-1}$ represents optionally substituted pyridyl and
R$^2$ has the meanings given in the definition of the invention.

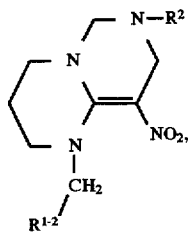
(Id)

in which
R$^{1-2}$ represents optionally substituted thiazolyl and
R$^2$ has the meanings given in the definition of the invention.

Preferred compounds according to the invention are also substance groups of the formulae (Ia-1), (Ib-1), (Ic-1) and (Id-1):

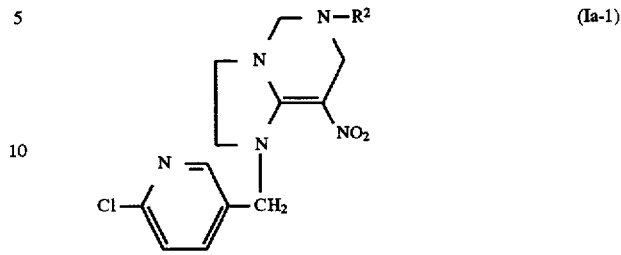
(Ia-1)

in which
R$^2$ represents the abovementioned general, preferred and particularly preferred meanings.

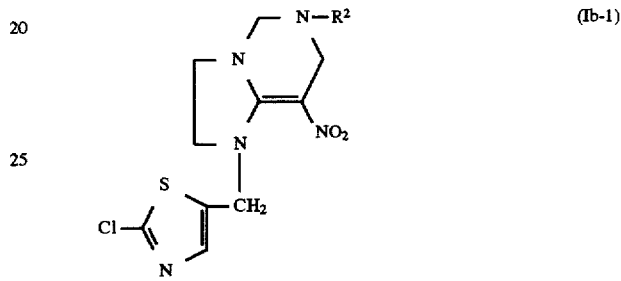
(Ib-1)

in which
R$^2$ represents the abovementioned general, preferred and particularly preferred meanings.

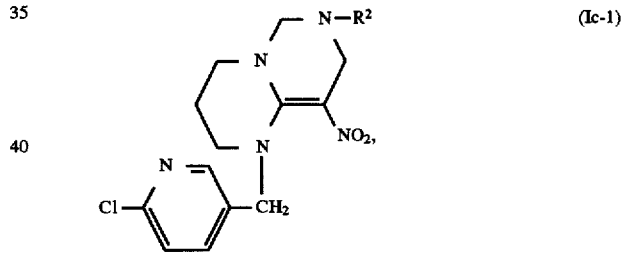
(Ic-1)

in which
R$^2$ represents the abovementioned general, preferred and particularly preferred meanings.

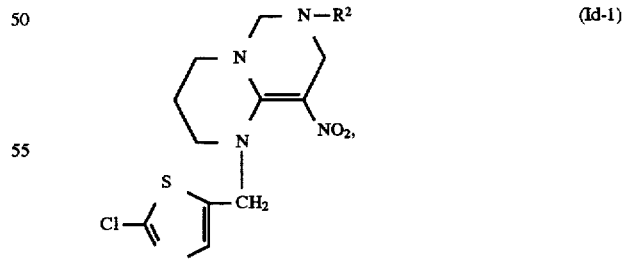
(Id-1)

in which
R$^2$ represents the abovementioned general, preferred and particularly preferred meanings.

Examples of the novel compounds according to the invention, in addition to the Preparation Examples, are listed in Tables a to d:

TABLE a
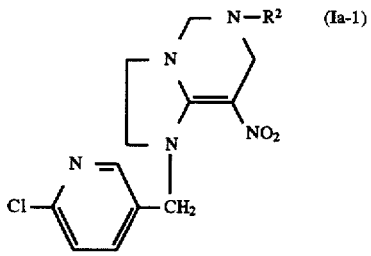
(Ia-1)
| R² | R² | R² |
|---|---|---|
| 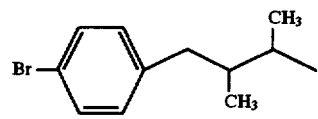 | 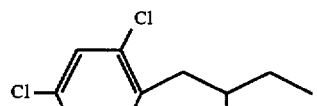 | 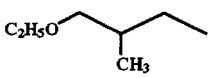 |
| 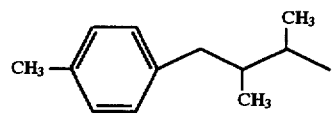 |  | 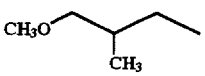 |
| 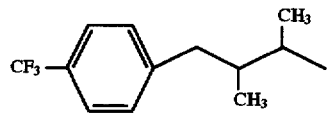 | 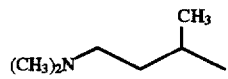 |  |
| 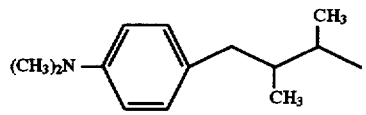 | 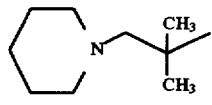 | 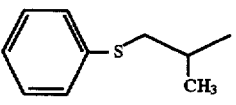 |
| 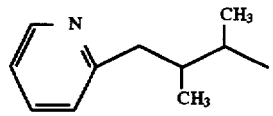 | 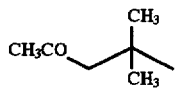 | 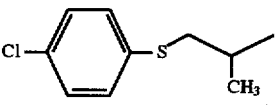 |
| 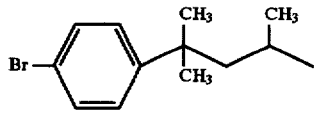 | 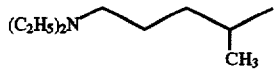 | 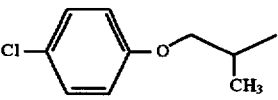 |
| 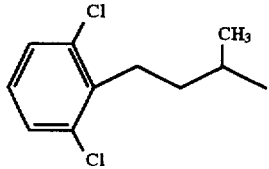 | 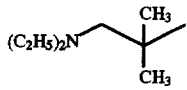 | 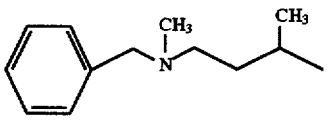 |
| 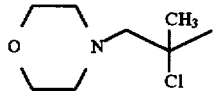 | 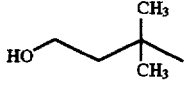 | 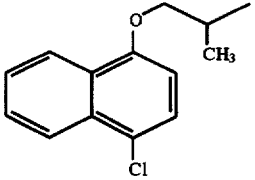 |

TABLE a-continued
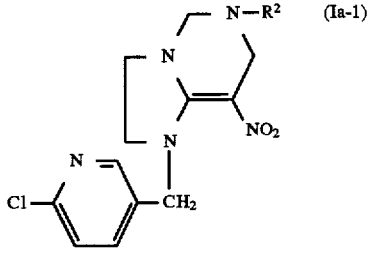
| R² | R² | R² |
|---|---|---|
| 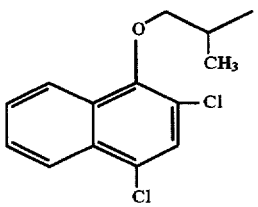 | 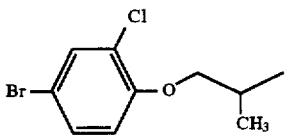 | 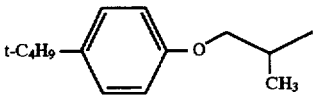 |
| 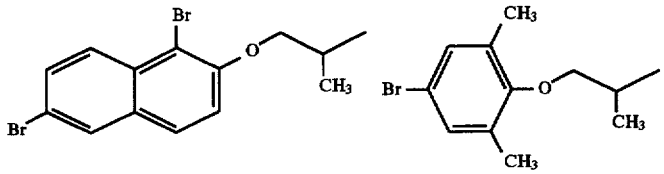 | 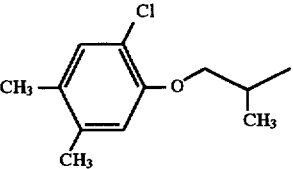 | 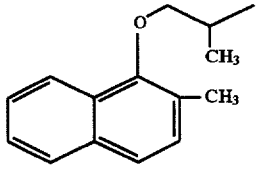 |
| 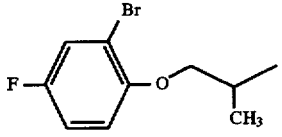 | 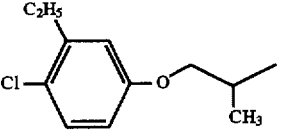 | 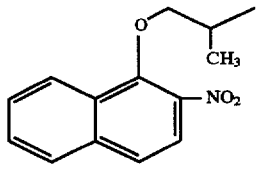 |
| 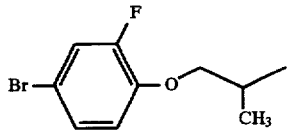 | 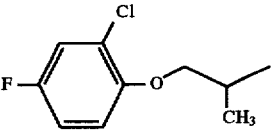 | 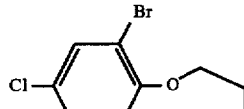 |
| 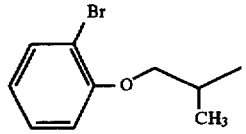 | | |

TABLE b (structure Ib-1: chlorothiazolylmethyl-substituted nitro-imino perhydrodiazepine with N–R²)

| R² | R² | R² |
|---|---|---|
| PhCH₂CH(CH₃)CH(CH₃)₂ | 3-Pyridyl-CH₂CH(CH₃)CH(CH₃)₂ | CH₃O–C(CH₃)(C₂H₅)– |
| 2-Cl-C₆H₄-CH₂CH(CH₃)CH(CH₃)₂ | 2-Pyridyl-CH₂CH(CH₃)CH(CH₃)₂ | (CH₃)₂N–CH₂CH₂CH(CH₃)₂ |
| 3-Cl-C₆H₄-CH₂CH(CH₃)CH(CH₃)₂ | 4-Br-C₆H₄-CH₂C(CH₃)₂CH(CH₃)₂ | Piperidinyl–CH₂C(CH₃)₂CH₃ |
| 4-F-C₆H₄-CH₂CH(CH₃)CH(CH₃)₂ | 2,3-Cl₂-C₆H₃-CH₂CH₂CH(CH₃)₂ | Piperidinyl–C(CH₃)(C₂H₅)– |
| 4-Br-C₆H₄-CH₂CH(CH₃)CH(CH₃)₂ | Morpholinyl–CH₂C(CH₃)₂CH₃ | Morpholinyl–CH₂CH₂C(CH₃)₃ |
| 4-CH₃-C₆H₄-CH₂CH(CH₃)CH(CH₃)₂ | 2,4-Cl₂-C₆H₃-CH₂CH(CH₃)C₂H₅ | F-CH₂-C(CH₃)(C₂H₅)– |
| 4-CF₃-C₆H₄-CH₂CH(CH₃)CH(CH₃)₂ | 4-CH₃-C₆H₄-CH₂CH₂CH(CH₃)₂ | (C₂H₅)NH–CH₂CH₂CH₂CH(CH₃)₂ |
| 4-(CH₃)₂N-C₆H₄-CH₂CH(CH₃)CH(CH₃)₂ | HC≡C–C(CH₃)₃ | (C₂H₅)NH–CH₂C(CH₃)₂C₂H₅ |
| 4-Pyridyl-CH₂CH(CH₃)CH(CH₃)₂ | (CH₃)₂N–CH₂C(CH₃)(C₂H₅)– | HO-CH₂CH₂C(CH₃)₂CH₃ |

TABLE b-continued (Ib-1) structure shown with R² substituents below.

| R² | R² | R² |
|---|---|---|
| C₂H₅O-CH(CH₃)-CH₂CH₃ (2-methylbutyl ethyl ether) | 4-Cl-C₆H₄-O-CH₂-CH(CH₃)₂ | 4-Br-2,6-(CH₃)₂-C₆H₂-O-CH₂-CH(CH₃)₂ |
| CH₃O-CH(CH₃)-CH₂CH₃ | PhCH₂-N(CH₃)-CH₂CH₂-CH(CH₃)₂ | 2-Br-4-F-C₆H₃-O-CH₂-CH(CH₃)₂ |
| C₂H₅O-CH₂-CH(CH₃)₂ | PhCH₂-N(C₂H₅)-CH₂CH₂CH(CH₃)-CH₃ | 2-F-4-Br-C₆H₃-O-CH₂-CH(CH₃)₂ |
| pyrazole-N-CH₂-C(CH₃)₂-... (hydrazone) | 2-pyridyl-O-CH₂-C(CH₃)₃ | 2-Br-C₆H₄-O-CH₂-CH(CH₃)₂ |
| 3,4-(CH₃)₂-C₆H₃-O-CH₂-CH(CH₃)₂ | 4-Cl-naphthyl-1-O-CH₂-CH(CH₃)₂ | 4-t-C₄H₉-C₆H₄-O-CH₂-CH(CH₃)₂ |
| 2-OCH₃-C₆H₄-O-CH₂-CH(CH₃)₂ | 2,4-di-Cl-naphthyl-1-O-CH₂-CH(CH₃)₂ | 2-Cl-4,5(or similar)-(CH₃)₂-C₆H₂-O-CH₂-CH(CH₃)₂ |
| 2,3-(CH₃)₂-C₆H₃-O-CH₂-CH(CH₃)₂ | 1,6-di-Br-naphthyl-2-O-CH₂-CH(CH₃)₂ | 2-C₂H₅-4-Cl-C₆H₃-O-CH₂-CH(CH₃)₂ |

TABLE b-continued
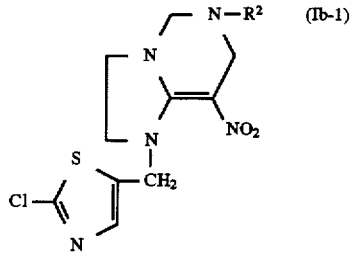 (Ib-1)
| R² | R² | R² |
|---|---|---|
| 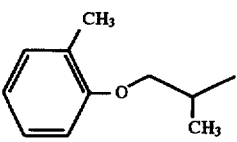 | 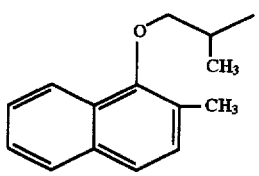 | 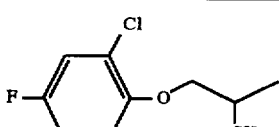 |
| 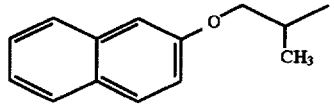 | 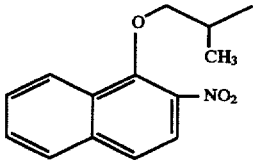 | |
| 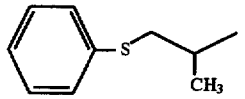 | 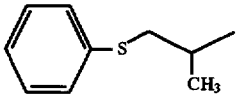 | |
| 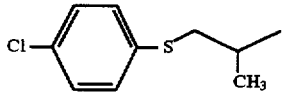 | 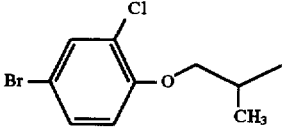 | |
TABLE c
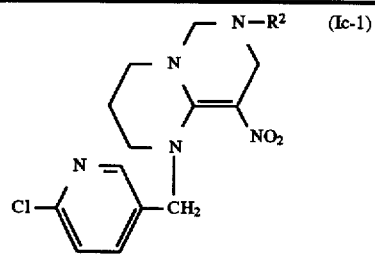 (Ic-1)
| R² | R² | R² |
|---|---|---|
| 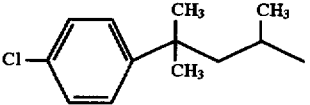 | 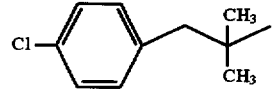 | 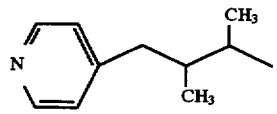 |
| 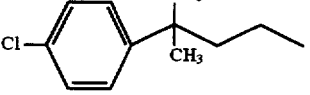 | 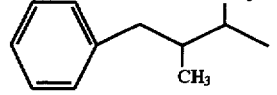 | 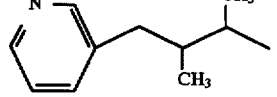 |

TABLE c-continued
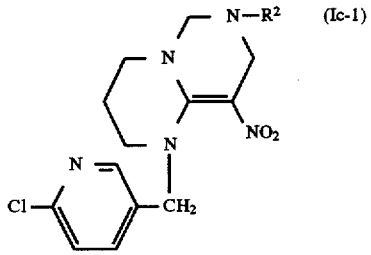 (Ic-1)
| R² | R² | R² |
|---|---|---|
| 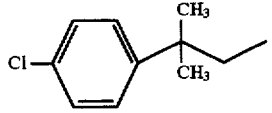 | 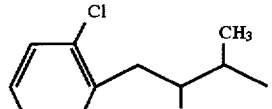 | 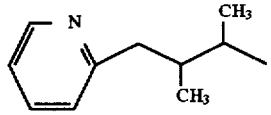 |
| 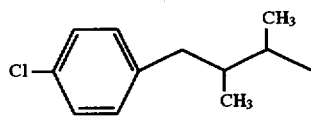 | 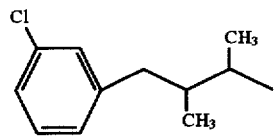 | 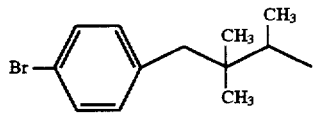 |
| 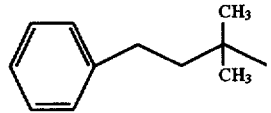 | 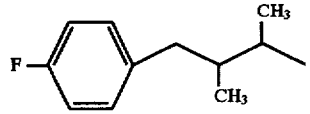 | 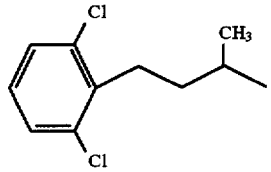 |
| 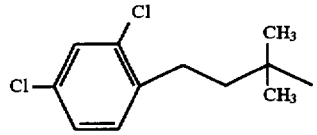 | 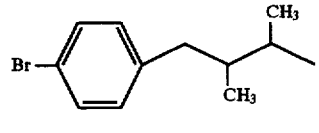 | 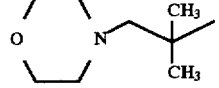 |
| 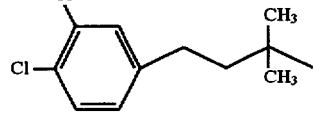 | 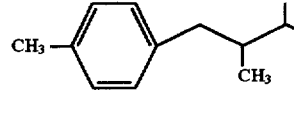 | 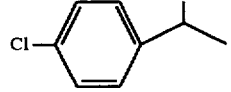 |
| 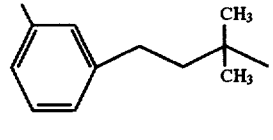 | 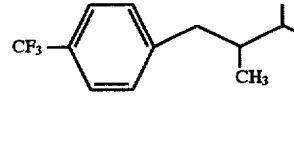 | 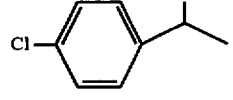 |
| 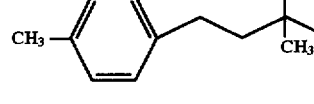 | 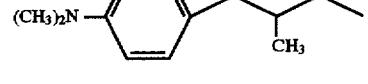 | 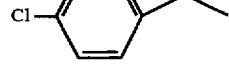 |
|  | 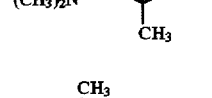 | 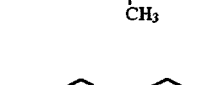 |
| 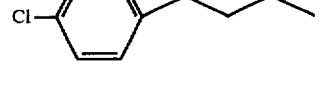 | 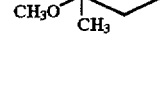 | 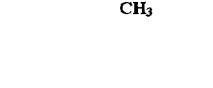 |

TABLE c-continued
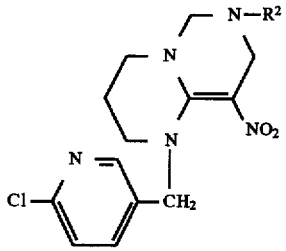 (Ic-1)
| R² | R² | R² |
|---|---|---|

TABLE c-continued
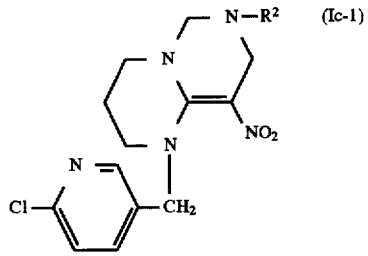 (Ic-1)

TABLE c-continued
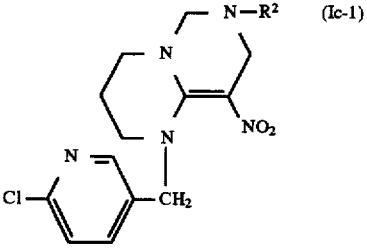
| $R^2$ | $R^2$ | $R^2$ |
|---|---|---|
| 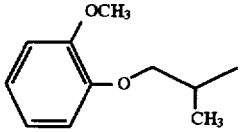 | 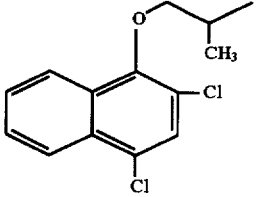 | 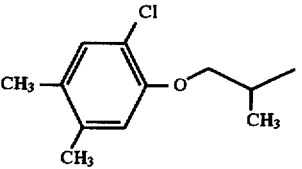 |
| 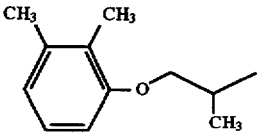 | 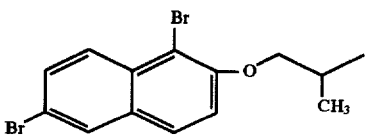 | 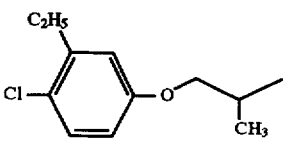 |
| 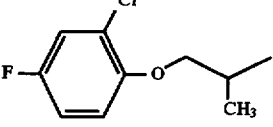 | | |
TABLE d
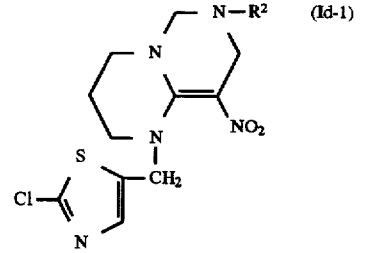
| $R^2$ | $R^2$ | $R^2$ |
|---|---|---|
| 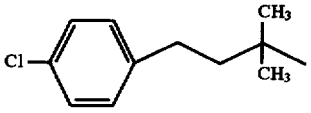 | 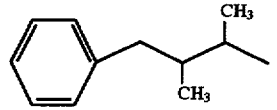 | 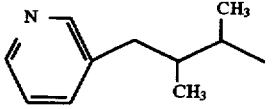 |
| 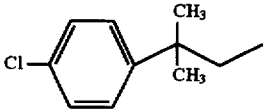 | 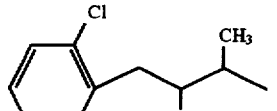 | 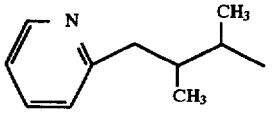 |
| 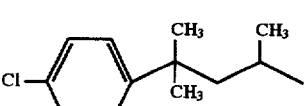 |  | 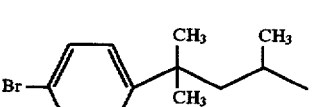 |

TABLE d-continued
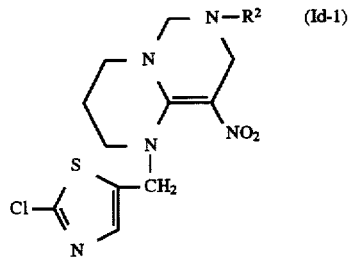 (Id-1)
| R² | R² | R² |
|---|---|---|
| 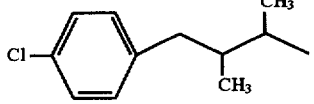 | 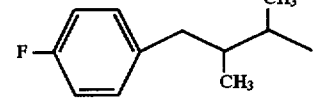 | 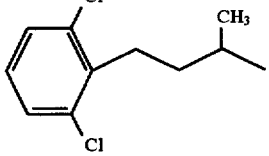 |
| 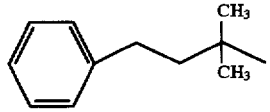 | 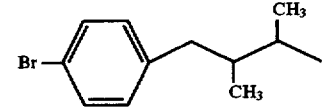 | 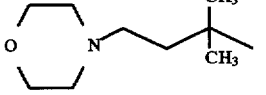 |
| 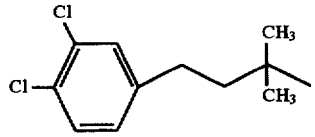 | 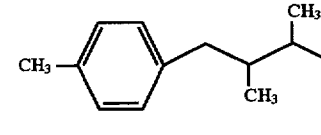 | 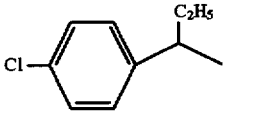 |
| 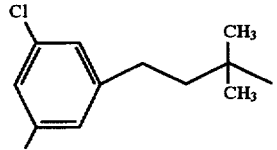 | 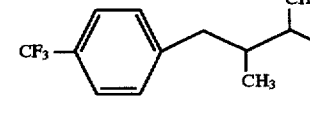 | 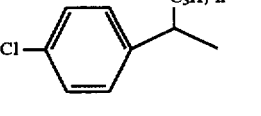 |
| 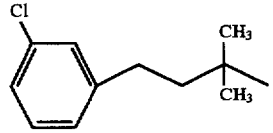 | 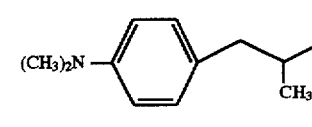 | 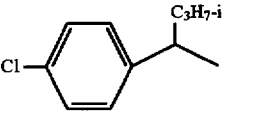 |
| 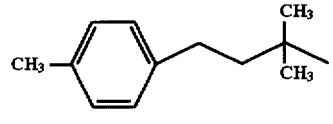 | 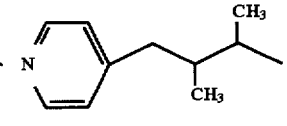 | 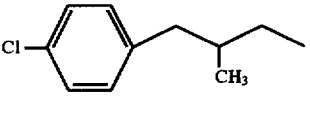 |
| 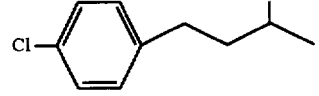 | 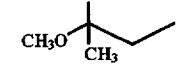 | 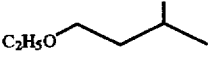 |
| 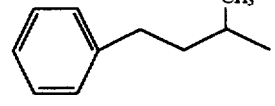 | 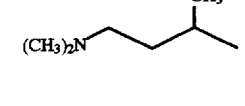 | 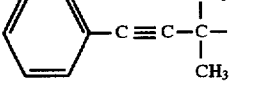 |
| 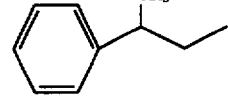 | 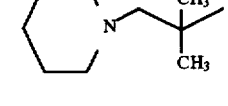 | 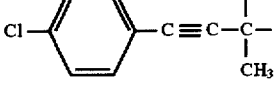 |

TABLE d-continued (structure Id-1 with chlorothiazolyl-CH2 group and N-R² substituent on nitroguanidine-like core)

| R² | R² | R² |
|---|---|---|
| 3-CF₃-C₆H₄-CH₂-CH(CH₃)₂ | 1-piperidinyl-C(CH₃)(C₂H₅)CH₃ | 3,4-Cl₂-C₆H₃-C≡C-C(CH₃)₃ |
| 3,4-Cl₂-C₆H₃-CH₂-CH(CH₃)₂ | CH₃OCH₂-C(CH₃)₂-CH₃ | 3,5-Cl₂-C₆H₃-C≡C-C(CH₃)₃ |
| 4-CF₃-C₆H₄-CH₂-CH(CH₃)₂ | FCH₂-C(CH₃)(C₂H₅) | 3-Cl-C₆H₄-C≡C-C(CH₃)₃ |
| 2,4-Cl₂-C₆H₃-CH₂-CH(CH₃)C₂H₅ | (C₂H₅)NH-CH₂CH₂CH₂-CH(CH₃)₂ | 4-NC-C₆H₄-C≡C-C(CH₃)₃ |
| 4-CH₃-C₆H₄-CH₂-CH(CH₃)₂ | (C₂H₅)₂N-CH₂-C(CH₃)₃ | 4-t-C₄H₉-C₆H₄-C≡C-C(CH₃)₃ |
| HC≡C-C(CH₃)₃ | C₂H₅O-CH₂-CH(CH₃)C₂H₅ | 4-CF₃-C₆H₄-C≡C-C(CH₃)₃ |
| (CH₃)₂N-CH₂-C(CH₃)₂C₂H₅ | CH₃O-CH₂-CH(CH₃)C₂H₅ | 4-CH₃-C₆H₄-C≡C-C(CH₃)₃ |
| 3,4-F₂-C₆H₃-C≡C-C(CH₃)₃ | C₆H₅-S-CH₂-CH(CH₃)₂ | 2-Br-4-Cl-C₆H₃-O-CH₂-CH(CH₃)₂ |
| 3-thienyl-C≡C-C(CH₃)₃ | 4-Cl-C₆H₄-S-CH₂-CH(CH₃)₂ | 2-Cl-4-Br-C₆H₃-O-CH₂-CH(CH₃)₂ |

TABLE d-continued
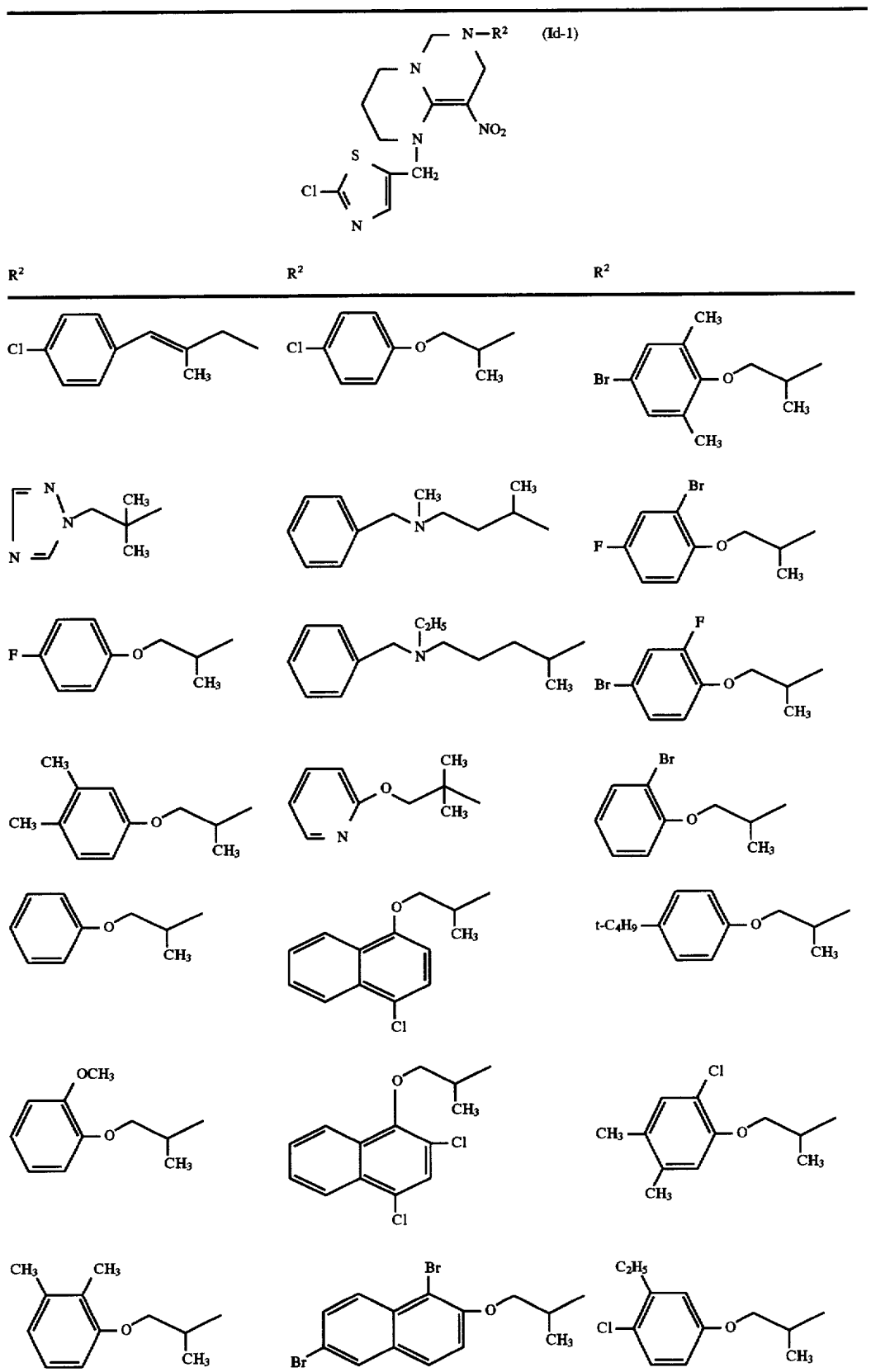

TABLE d-continued

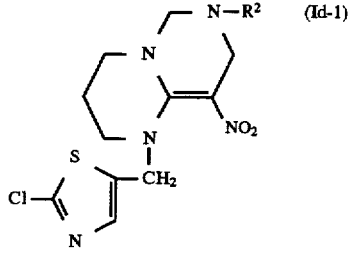

| R² | R² | R² |
|---|---|---|
| 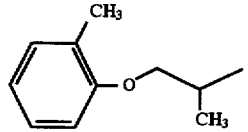 | 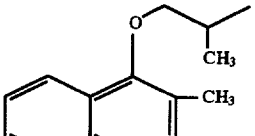 | 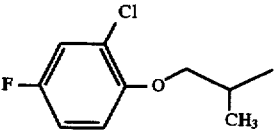 |
| 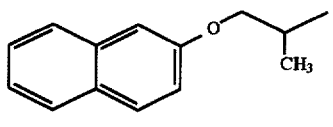 | 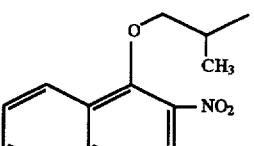 | |

If the process according to the invention is carried out using, for example, 3-(2-chloropyridin-5-yl-methyl)-2-nitromethylene-imidazolidine, 2-amino-4-methyl-4(4-chlorophenyl)-pentane and 2 mol of formaldehyde, then the course of the reaction can be outlined by the following equation:

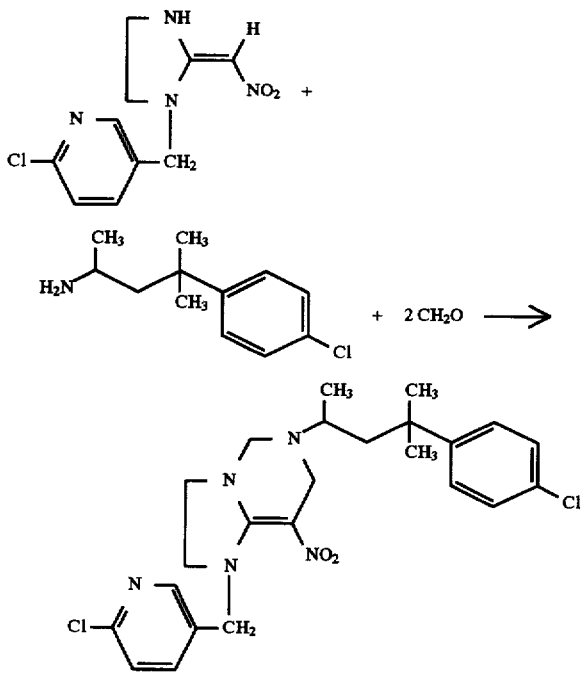

A general definition of the nitromethylene derivatives to be used as starting materials in the process according to the invention is given by the formula (II). In the formula (II), $R^1$ and n preferably or particularly preferably have those meanings which have already been given above, in connection with the description of the compounds of the formula (I) according to the invention, as preferable or particularly preferable, respectively, for $R^1$ and n.

The nitromethylene derivatives of the formula (II) are known and/or can be prepared by known methods (cf. e.g. DE-A 2 514 402, EP-A 136 636, EP-A 154 178 and EP-A 163 855).

A general definition of the amines also to be used as starting materials in the process according to the invention is given by the formula (III). In the formula (III), $R^2$ preferably or particularly preferably has that meaning which has already been given above, in connection with the description of the compounds of the formula (I) according to the invention, as preferable or particularly preferable, respectively, for $R^2$.

The amines of the formula (III) are generally known compounds of organic chemistry.

It is also possible to convert the compounds of the formula (I) into adducts with acids.

The acids which can be subjected to addition include, preferably, hydrohalic acids, for example hydrochloric acid and hydrobromic acid, especially hydrochloric acid, and also phosphoric acid, sulphuric acid, nitric acid, acetic acid, oxalic acid, malonic acid, succinic acid, malic acid, tartaric acid, maleic acid, fumaric acid, methanesulphonic acid, benzoic acid, substituted benzoic acids, formic acid, chloroacetic acid, toluenesulphonic, benzenesulphonic acid, trichloroacetic acid, phthalic acid, naphthalenesulphonic acid, nicotinic acid, citric acid and ascorbic acid.

The process according to the invention for the preparation of the novel compounds of the formula (I) is preferably carried out using diluents. Suitable diluents in this context are water and organic solvents which are inert for the reaction. These include, preferably aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, alcohols such as methanol, ethanol, n-propanol and isopropanol. Mixtures of alcohols and water are preferably employed.

The process according to the invention is optionally carried out in the presence of acidic, non-oxidizing catalysts. Hydrohalic acids such as hydrochloric acid and hydrobromic acid, phosphoric acid, lower carboxylic acids such as acetic acid and propionic acid, have proved particularly suitable.

The reaction temperatures in the process according to the invention can be varied within a relatively large range. It is in general carried out at temperatures between −20° C. and +120° C., preferably at temperatures between 0° C. and +80° C.

The process according to the invention is in general carried out under atmospheric pressure. However, it is also possible to work under elevated or reduced pressure.

To carry out the process according to the invention, from 1 to 1.5 mol, preferably from 1 to 1.2 mol, of amine of the (formula III) and from 2 to 4 mol, preferably from 2 to 3 mol of formaldehyde are employed per mole of nitromethylene derivative of the formula (II).

The amines of the formula (III) can optionally be employed as aqueous solutions. When using gaseous amines of the formula (III), these compounds can be passed through the mixture comprising diluent, compounds of the formula (II) and formaldehyde. For the process according to the invention, formaldehyde is employed in aqueous solution. The reactions are in general carried out in a suitable diluent, and the reaction mixture is stirred for several hours at the particular temperature required. In the process according to the invention, the reaction mixture is in each case worked up by customary methods.

The acid addition salts of the compounds of the formula (I) can be obtained in a simple manner by customary methods of forming salts, for example by dissolving a compound of the formula (I) in a suitable inert solvent and adding the acid, for example hydrochloric acid, and can be isolated in a known manner, for example by filtration, and can if desired be purified by washing with an inert organic solvent.

With good tolerance by plants and favourable toxicity to warm-blooded animals, the active compounds are suitable for combating animal pests, especially insects, arachnids and nematodes, which are encountered in agriculture, in forestry, in the protection of stored products and of materials, and in the hygiene sector. They can preferably be used as plant protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Caprocapsa pomonella,* Pieris spp., Chilo spp., *Pyrausta nubilalis, Ephestia kuehniella, Galleria mellonella, Tineola bissellielia, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include, for example, Pratylenchus spp., *Radopholus similis, Ditylenchus dipsaci, Tylenchulus semipenetrans*, Heterodera spp., Globodera spp., Meloidogyne spp., Aphelenchoides spp., Longidorus spp., Xiphinema spp. and Trichodorus spp.

The compounds of the formula (I) according to the invention are distinguished in particular by a high insecticidal and acaricidal activity.

They can be employed with particular success for combating insects which damage plants, for example against the larvae of the mustard beetle (*Phaedon cochlaeriae*), the caterpillars of the owlet moth (*Spodoptera frugiperda* or *exigua*), the cotton bollworm (*Heliothis armigera*), the rice green leafhopper (*Nephotettix cincticeps*) and the peach aphid (*Mycus persicae*) or for combating plant-damaging mites, for example against the common spider mite or two-spotted spider mite (*Tetranychus urticae*).

Furthermore, they show a good soil-insecticidal action, for example against *Diabrotica balteata* larvae, and a good root-systemic action, for example against *Aphis fabae*.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound and very fine capsules in polymeric substances.

These formulations are produced in a known manner, for example by mixing the active compounds with extenders, that is liquid solvents and/or solid carriers, optionally with the use of surface-active agents, that is, emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, minerals and plant oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents these are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound according to the invention can, in its commercially customary formulations and in the use forms prepared from these formulations, be present as a mixture with other active compounds, such as insecticides, attractants, sterilants, bactericides, acaricides, nematicides, fungicides, growth regulators or herbicides. The insecticides include, for example, phosphates, carbamates, carboxylates, chlorinated hydrocarbons, phenylureas, substances produced by microorganisms, etc.

Examples of particularly advantageous components for the mixtures are the following compounds:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6 dichloro-N-(4-trifluoromethylbenzyl)benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino [alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazole, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulfur and sulfur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184 699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyradaphenthion, pyresmethrin, pyrethrum, pyridaben, pyrimidifen, pyriproxifen, quinalphos,

RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Also possible is a mixture with other known active compounds, such as herbicides, or with fertilizers and growth regulators.

The active compounds according to the invention can additionally be present in their commercially customary formulations, and in the use forms prepared from these formulations, in a mixture with synergists. Synergists are compounds by means of which the action of the active compounds is increased without the added synergist itself necessarily being active.

The content of active compound in the use forms prepared from the commercially customary formulations can vary within wide ranges. The active-compound concentration of the use forms can be from 0.0000001 to 95% by weight of active compound, preferably between 0.0001 and 1% by weight.

Application is effected in a customary manner which is adapted to the use forms.

When used against hygiene pests and stored-products pests, the active compound is notable for an outstanding residual action on wood and clay, and for good alkali stability on limed substrates.

The active compounds according to the invention are active not only against plant pests, hygiene pests and stored-product pests but also, in the field of veterinary medicine, against animal parasites (ectoparasites) such as scaly ticks, Argasidae, scab mites, Trombidae, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp., Felicola spp.

From the order of the Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp., Melophagus spp.

From the order of the Siphonapterida, for example, Pulex spp., Ctenocephalides spp., Xenopsylla spp., Ceratophyllus spp.

From the order of the Heteropterida, for example, Cimex spp., Triatoma spp., Rhodnius spp., Panstrongylus spp.

From the order of the Blattarida, for example, *Blatta orientalis, Periplaneta americana, Blattela germanica*, Supella spp.

From the sub-class of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp., Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp., Laminosioptes spp.

For example, they show an outstanding activity against cockroaches, for example *Periplaneta americana*, and against flies, for example *Musca domestica*.

They also show a development-inhibiting action, for example against fly larvae of *Lucilia cuprina*.

The active compounds of the formula (I) according to the invention are also suitable for combating arthropods which infest agricultural productive animals, for example cattle, sheep, goats, horses, pigs, donkeys, camels, buffalo, rabbits, chickens, turkeys, ducks, geese and bees, and other domestic animals, for example dogs, cats, cage birds and aquarium fish, and also so-called experimental animals, for example hamsters, guinea pigs, rats and mice. By combating these arthropods the intention is to diminish cases of death and reductions in yield (in the case of meat, milk, wool, hides, eggs, honey, etc.), so that the use of the active compounds according to the invention enables the keeping of animals to be more economic and more simple.

The active compounds according to the invention are used in the veterinary sector in a known manner by enteral administration in the form of, for example, tablets, capsules, potions, drenches, granules, pastes, boll, the feed-through process and suppositories, by parenteral administration, for example by injections (intramuscular, subcutaneous, intravenous, intraperitoneal, etc.), by implants, by nasal administration, by dermal application in the form of, for example, dipping or bathing, spraying, pouring on and spotting on, washing, and powdering, and also with the aid of shaped articles containing active compound, such as collars, ear tags, tail tags, limb bands, halters, marking devices, etc.

When used for livestock, poultry, domestic animals etc., the active compounds of the formula (I) can be used as formulations (for example powders, emulsions, flowable compositions) which contain the active compounds in a quantity of from 1 to 80% by weight, either directly or after dilution by a factor of from 100 to 10 000, or they may be used as a chemical bath.

It has additionally been found that the compounds of the formula (I) according to the invention have a potent insecticidal action against insects which destroy industrial materials.

The following insects may be mentioned by way of example and preference, but not by way of limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec. Tryptodendron spec. *Apate monachus, Bostrychus capucins, Heterobostrychus brunneus,* Sinoxylon spec. *Dinoderus minutus*

Dermaptera, such as

*Sirex juvencus, Urocerus gigas, Urocerus gigas taignus, Urocerus augur*

Termites, such as

*Kalotermes flavicollis, Cryptotermes brevis, Heterotermes indicola, Reticulitermes flavipes, Reticulitermes santonenis, Reticulitermes lucifugus, Mastotermes darwiniensis, Zootermopsis nevadensis, Coptotermes formosanus.*

Bristle tails, such as *Lepisma saccharina.*

Industrial materials are to be understood in the present context as meaning non-living materials such as, preferably, plastics, adhesives, sizes, papers and boards, leather, wood and derived timber products, and coating compositions.

The material to be protected against attack by insects is, with very particular preference, wood and derived timber products.

Wood and derived timber products which can be protected by the agent according to the invention or by compositions comprising it are to be understood as meaning, for example, construction timber, wooden beams, railway sleepers, bridge components, jellies, wooden vehicles, crates, pallets, containers, telephone poles, wooden facings, wooden windows and doors, plywood, chipboard, joinery works, or wood products which, quite generally, are used in construction or joinery.

The active compounds can be used as such, in the form of concentrates or generally customary formulations, such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellant, siccatives and UV stabilizers if desired, and, also if desired, dyes and pigments, and further processing auxiliaries.

The insecticidal compositions or concentrates used for protecting wood and wood materials comprise the active compound according to the invention in a concentration of from 0.0001 to 95% by weight, in particular from 0.001 to 60% by weight.

The quantity of the compositions or concentrates employed depends on the species and on the incidence of the insects and on the medium. The optimum quantity for use can be determined in each case, upon use, by a series of tests. However, in general it is sufficient to employ from 0.0001 to 20% by weight, preferably from 0.001 to 10% by weight, of the active compound, based on the material to be protected.

The solvent and/or diluent used is an organic chemical solvent or solvent mixture and/or an oily or oil-like organic chemical solvent or solvent mixture of low volatility and/or a polar organic chemical solvent or solvent mixture and/or water and, if desired, an emulsifier and/or wetting agent.

The organic chemical solvents employed are preferably oily or oil-like solvents having an evaporation number of above 35 and a flash point of above 30° C., preferably above 45° C. Substances used as such oily and oil-like solvents of low volatility which are insoluble in water are appropriate mineral oils or their aromatic fractions or sol{rent mixtures which comprise mineral oil, preferably white spirit petroleum and/or alkylbenzene.

It is advantageous to use mineral oils having a boiling range of from 170° to 220° C., white spirit with a boiling range of from 170° to 220° C., spindle oil with a boiling range of from 250° to 350° C., petroleum or aromatics with a boiling range of from 160° to 280° C., spirit of turpentine and the like.

In a preferred embodiment, the substances used are liquid aliphatic hydrocarbons having a boiling range of from 180° to 210° C. or high-boiling mixtures of aromatic and aliphatic hydrocarbons having a boiling range of from 180° to 220° C. and/or spindle oil and/or monochloronaphthalene, preferably α-monochloronaphthalene.

The organic oily or oil-like solvents of low volatility having an evaporation number of more of than 35 and a flash point above 30° C., preferably above 45° C., can be replaced in part by organic chemical solvents of high or medium volatility, with the proviso that the solvent mixture likewise has an evaporation number of above 35 and a flash point of above 30° C., preferably above 45° C., and that the insecticide/fungicide mixture is soluble or emulsifiable in this solvent mixture.

In a preferred embodiment, part of the organic chemical solvent or solvent mixture is replaced or an aliphatic polar organic chemical solvent or solvent mixture. Substances which are preferably used are aliphatic organic chemical solvents containing hydroxyl and/or ester and/or ether groups, for example glycol ethers, esters or the like.

Organic chemical binders which are used within the scope of the present invention are the binding, drying oils and/or synthetic resins which are known per se, can be diluted with water and/or are soluble, dispersible or emulsifiable in the organic chemical solvents employed, especially binders composed of or comprising an acrylate resin, a vinyl resin, for example polyvinyl acetate, a polyester resin, a polycondensation or polyaddition resin, a polyurethane resin, alkyd resin or modified alkyd resin, a phenolic resin, a hydrocarbon resin such as indenecoumarone resin, a silicone resin, drying vegetable oils and/or drying oils and/or physically drying binders based on a natural and/or synthetic resin.

The synthetic resin used as binder can be employed in the form of an emulsion, dispersion or solution. Substances which may also be employed as binders are bitumen or bituminous substances in quantities of up to 10% by weight. In addition it possible to employ dyes, pigments, water repellents, odoriferous substances and inhibitors or anticorrosion agents and the like which are known per se.

The composition or concentrate preferably comprises as organic chemical binder, in accordance with the invention, at least one alkyd resin or modified alkyd resin and/or a drying vegetable oil. According to the invention, alkyd resins having an oil content of more than 45% by weight, preferably 50 to 68% by weight, are used with preference.

The abovementioned binder can be replaced in whole or in part by a fixative (mixture) or a plasticizer (mixture). These additives are intended to prevent volatilization of the active compounds and crystallization or precipitation. They preferably replace from 0.01 to 30% of the binder (based on 100% of the binder employed).

The plasticizers are derived from the chemical classes of the phthalates, such as dibutyl phthalate, dioctyl phthalate or benzyl butyl phthalate, phosphates, such as tributyl phosphate, adipates, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic esters.

Fixatives are based chemically on polyvinyl alkyl ethers such as, for example, polyvinyl methyl ether or ketones, such as benzophenone or ethylenebenzophenone.

Another suitable solvent or diluent is, in particular, water, alone or in a mixture with one or more of the abovementioned organic chemical solvents or diluents, emulsifiers and dispersants.

Particularly effective protection of wood is afforded by means of industrial-scale impregnating processes, for example vacuum, double-vacuum or pressure processes.

If appropriate, the ready-to-use compositions can comprise other insecticides and, if desired, one or more other fungicides.

Additional co-components are preferably the insecticides and fungicides mentioned in Wo 94/29 268. The compounds mentioned in this document are an express part of the present application.

Co-components to which very particular preference is attached can be insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorfluanid, tolylfluanid, 3-iodo-2-propinyl butylcarbamate, N-octyl-isothiazolin-3-one and 4,5-dichloro-N-octylisothiazolin-3-one.

The preparation and use of the active compounds according to the invention can be seen from the examples which follow.

PREPARATION EXAMPLES

Example 1

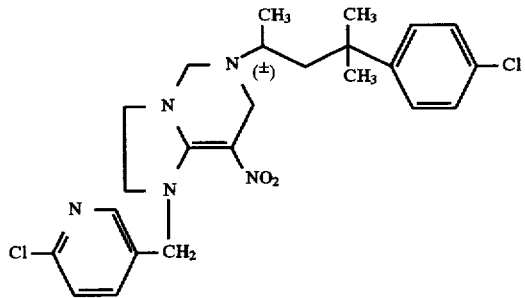

1.5 ml (0.02 mol) of 37% strength aqueous formaldehyde solution are added dropwise at room temperature to a mixture of 2.54 g (0.01 mol) of 3-(2-chloropyridin-5-yl-methyl)-2-nitromethylene-imidazolidine and 2.1 g (0.01 mol) of 2-amino-4-methyl-4(4-chlorophenyl)-pentane in 90 ml of ethanol and the mixture is heated under reflux for 3 hours. After cooling to room temperature, the solvent is removed in vacuo, ether is added to the residue, and the mixture is filtered with suction.

3.2 g (66% of theory) of 6,7-dihydro-6-[4-methyl-4-(4-chlorophenyl)-pent-2-yl]-8-nitro-(5H)-1-(2-chloropyridin-5-yl-methyl)-imidazolidino-[2,3-f]-pyrimidine are obtained of melting point 162° C.

Example 2

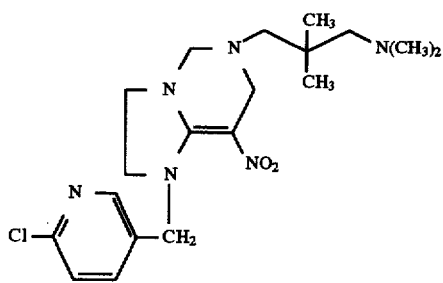

4.62 ml (0.0462 mol) of 37% strength aqueous formaldehyde solution are added dropwise at room temperature to a mixture of 5.9 g (0.0231 mol) of 3-(2-chloropyridin-5-yl-methyl)-2-nitromethylene-imidazolidine and 3.0 g (0.0231 mol) of 3-dimethylamino-2,2-dimethylpropylamine in 120 ml of ethanol and the mixture is heated under reflux for 3 hours. After cooling to room temperature, the solvent is removed in vacuo, the residue is stirred with ether and the mixture is filtered with suction.

6.9 g (73% of theory) of 6,7-dihydro-6-(3-dimethylamino-2,2-dimethylprop-1-yl)-8-nitro-(5H)-1-(2-chloropyridin-5-yl-methyl)-imidazolidino-[2,3-f]-pyrimidine are obtained of melting point 136° C.

Example 3

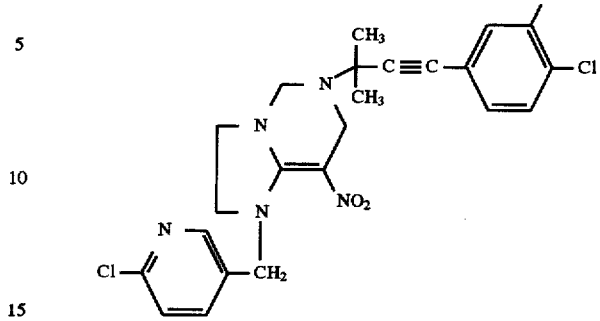

2.0 ml (0.02 mol) of 30% strength aqueous formaldehyde solution are added dropwise at room temperature to a mixture of 2.5 g (0.01 mol) of 3-(2-chloro-pyridin-5-yl-methyl)-2-nitromethylene-imidazolidine and 2.3 g (0.01 mol) of 2-amino-2-methyl-4-(3,4-dichlorophenyl)-but-3-ine in 90 ml of ethanol and the mixture is heated under reflux for 3 hours. After cooling to room temperature, the solvent is removed in vacuo, the residue is stirred with ether and the mixture is filtered with suction.

3.6 g (73% of theory) of 6,7-dihydro-6-[2-methyl-4-(3,4-dichlorophenyl)-but-3-in-2-yl]-8-nitro-(5H)-1-(2-chloropyridin-5-yl-methyl)-imidazolidino-[2,3-f]-pyrimidine are obtained of melting point 130° C.

By analogy with Examples 1 to 3 and in accordance with the general preparation instructions, the compounds of the formula (IA) indicated in the table below are obtained:

![Formula IA structure]

| Ex.-No. | $R^1$ | $R^2$ | m.p. (°C.) |
|---|---|---|---|
| 4 | 2-chloro-pyridin-5-yl | -C(CH₃)₂-CH₂-CH₂-CH₃ with 4-Cl-phenyl | 98 |
| 5 | 2-chloro-pyridin-5-yl | -C(CH₃)₂-CH₂-CH₃ with 4-Cl-phenyl | 167 |
| 6 | 2-chloro-pyridin-5-yl | -CH₂-CH(CH₃)-CH(CH₃)- with 4-Cl-phenyl (±) | 122 (decomp.) |

-continued

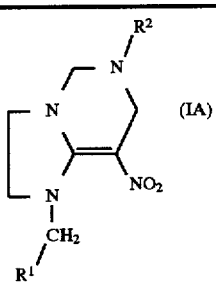

| Ex.-No. | R¹ | R² | m.p. (°C.) |
|---|---|---|---|
| 7 | 2-chloro-5-pyridyl | 3,3-dimethyl-3-phenylpropyl (CH₂CH₂C(CH₃)₂-phenyl) | 135 (decomp.) |
| 8 | 2-chloro-5-pyridyl | 2-(3,5-dichlorophenyl)-1,1-dimethylethyl group | 135 (decomp.) |
| 9 | 2-chloro-5-pyridyl | 2-(3,4-dichlorophenyl)-1,1-dimethylethyl group | 130 (decomp.) |
| 10 | 2-chloro-5-pyridyl | 2-(3-chlorophenyl)-1,1-dimethylethyl group | 135 (decomp.) |
| 11 | 2-chloro-5-pyridyl | 2-(4-methylphenyl)-1,1-dimethylethyl group | 120 (decomp.) |
| 12 | 2-chloro-5-pyridyl | 2-(4-chlorophenyl)-1,1-dimethyl | 88 |
| 13 | 2-chloro-5-pyridyl | 2-methyl-3-phenyl-butyl (±) | Oil |
| 14 | 2-chloro-5-pyridyl | 2-methyl-3-(2-chlorophenyl)butyl (±) | Oil |
| 15 | 2-chloro-5-pyridyl | 2-methyl-3-(3-chlorophenyl)butyl (±) | Oil |

-continued
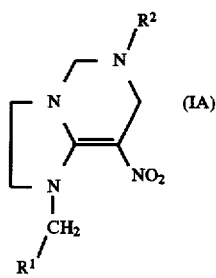
| Ex.-No. | R¹ | R² | m.p. (°C.) |
|---|---|---|---|
| 16 | 2-chloro-5-pyridyl | 4-F-C₆H₄-CH₂-CH(CH₃)-CH(CH₃)₂ (±) | Oil |
| 17 | 2-chloro-5-pyridyl | 3-pyridyl-CH₂-CH(CH₃)-CH(CH₃)₂ (±) | Oil |
| 18 | 2-chlorothiazol-5-yl | 4-Cl-C₆H₄-CH₂-C(CH₃)₃ | 65 |
| 19 | 2-chlorothiazol-5-yl | 4-Cl-C₆H₄-C(CH₃)₂-C₂H₅ | 70 |
| 20 | 2-chlorothiazol-5-yl | 4-Cl-C₆H₄-C(CH₃)₂-CH₂-CH(CH₃)₂ (±) | 69 |
| 21 | 2-chlorothiazol-5-yl | 4-Cl-C₆H₄-CH₂-CH(CH₃)-CH(CH₃)₂ (±) | 70 |
| 22 | 2-chlorothiazol-5-yl | C₆H₅-CH₂-CH₂-C(CH₃)₃ | 142 |
| 23 | 2-chlorothiazol-5-yl | 3,4-Cl₂-C₆H₃-CH₂-CH₂-C(CH₃)₃ | 120 |

-continued
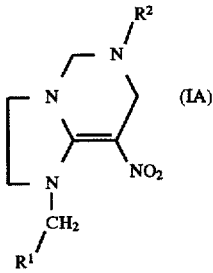
| Ex.-No. | R¹ | R² | m.p. (°C.) |
|---|---|---|---|
| 24 | 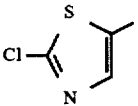 | 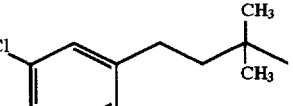 | 141 |
| 25 | 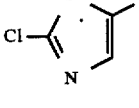 | 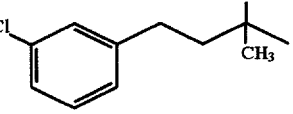 | 105 |
| 26 | 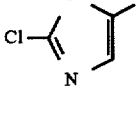 | 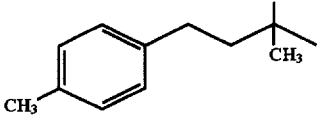 | 108 |
| 27 | 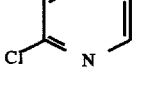 | 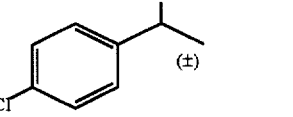 | 135 |
| 28 | 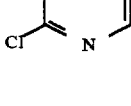 | 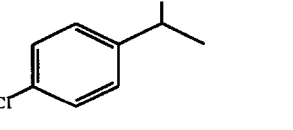 | Oil |
| 29 | 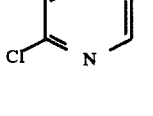 | 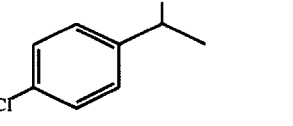 | 190 |
| 30 | 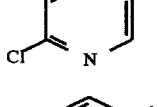 | 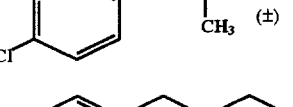 | 30 |
| 31 | 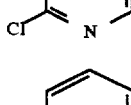 | 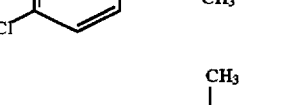 | 178 |
| 32 | 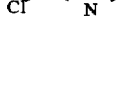 |  | 169 |

-continued

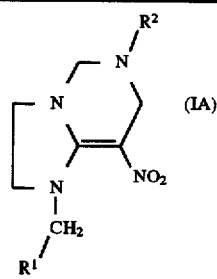

| Ex.-No. | R¹ | R² | m.p. (°C.) |
|---|---|---|---|
| 33 | 2-chloro-5-pyridyl | 1-phenylpropyl (±) (sec-butylbenzene) | 162 |
| 34 | 2-chloro-5-pyridyl | 3-(trifluoromethyl)phenyl isopentyl (±) | 140 |
| 35 | 2-chloro-5-pyridyl | 3,4-dichlorophenyl isopentyl (±) | 143 |
| 36 | 2-chloro-5-pyridyl | 4-(trifluoromethyl)phenyl isopentyl (±) | 190 |
| 37 | 2-chloro-5-thiazolyl | 1-(4-chlorophenyl)propyl (C₂H₅) | 67 |
| 38 | 2-chloro-5-thiazolyl | 1-(4-chlorophenyl)butyl (C₃H₇-n) | 140 |
| 39 | 2-chloro-5-thiazolyl | 1-(4-chlorophenyl)-2-methylpropyl (C₃H₇-i) | 169 |
| 40 | 2-chloro-5-thiazolyl | 2-methyl-1-(4-chlorophenyl)butyl (±) | Oil |
| 41 | 2-chloro-5-thiazolyl | 3-(4-chlorophenyl)-2-methylpropyl (±) | 94 |

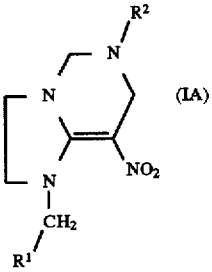

-continued
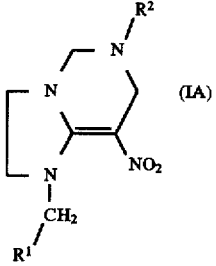 (IA)
| Ex.-No. | R¹ | R² | m.p. (°C.) |
|---|---|---|---|
| 52 | 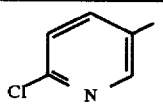 | 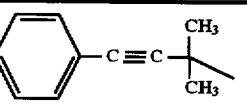 | 93 |
| 53 | 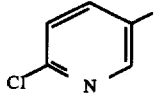 | 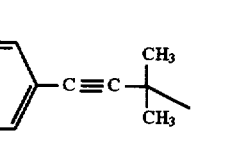 | 67 |
| 54 | 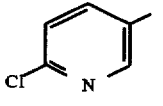 | 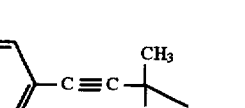 | 55 |
| 55 | 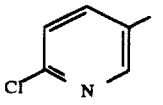 | 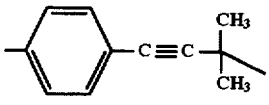 | 73 |
| 56 | 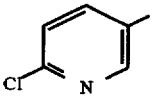 | 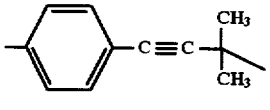 | 73 |
| 57 | 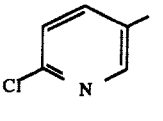 | 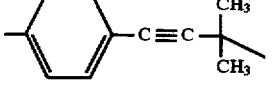 | 65 |
| 58 | 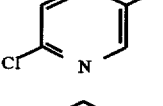 | 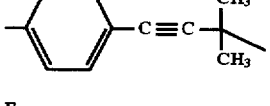 | 70 |
| 59 | 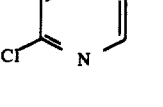 | 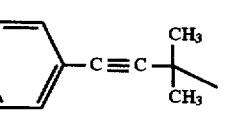 | 69 |
| 60 | 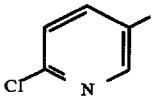 | 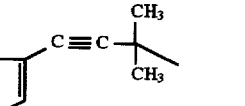 | 62 |
| 61 | 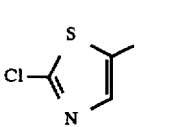 | 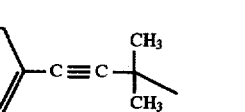 | 63 |

-continued
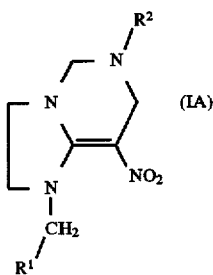
| Ex.-No. | R¹ | R² | m.p. (°C.) |
|---|---|---|---|
| 62 | 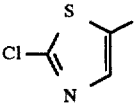 | 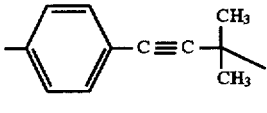 | 61 |
| 63 | 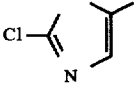 | 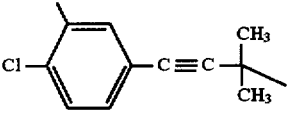 | 170 |
| 64 | 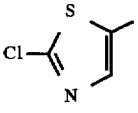 | 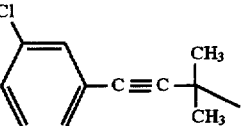 | 170 |
| 65 | 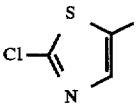 | 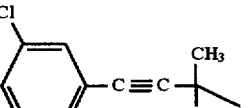 | 72 |
| 66 | 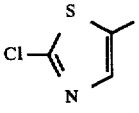 | 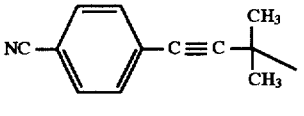 | 78 |
| 67 | 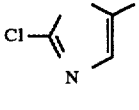 | 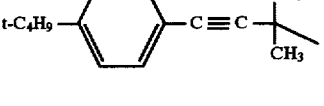 | 80 |
| 68 | 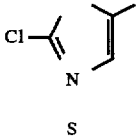 | 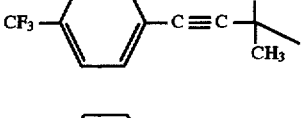 | 65 |
| 69 | 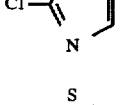 | 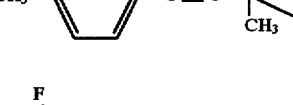 | 62 |
| 70 | 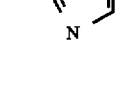 | 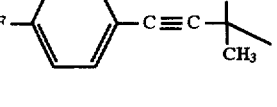 | 145 |

-continued
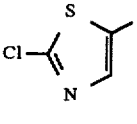
| Ex.-No. | R¹ | R² | m.p. (°C.) |
|---|---|---|---|
| 71 | 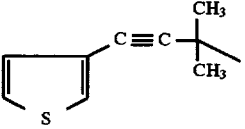 | 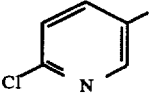 | 68 |
| 72 | 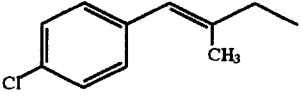 | 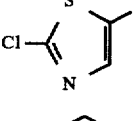 | 189 |
| 73 | 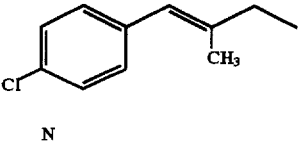 | 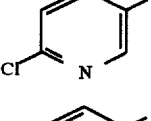 | 137 |
| 74 | 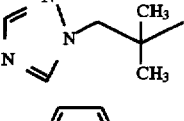 | 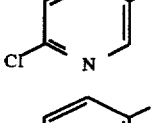 | 181 |
| 75 | 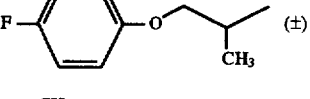 | 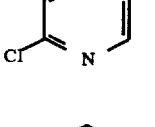 (±) | 166 |
| 76 | 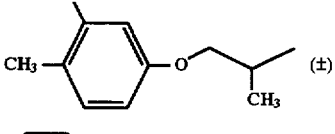 | 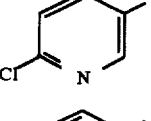 (±) | 122 |
| 77 | 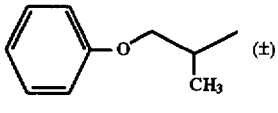 | 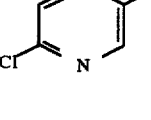 (±) | 123 |
| 78 | 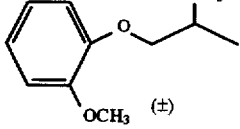 | 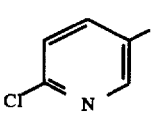 (±) | 108 |
| 79 | 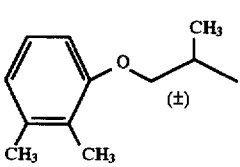 | 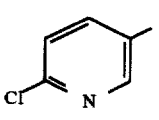 (±) | 139 |
| 80 | 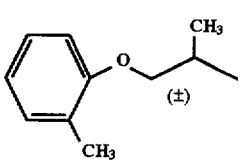 | | 126 |

-continued

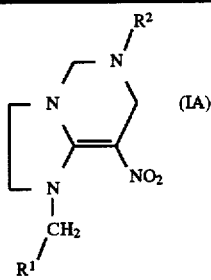

| Ex.-No. | R¹ | R² | m.p. (°C.) |
|---|---|---|---|
| 81 | 2-chloro-pyridin-5-yl-methyl | 2-naphthyloxy-propyl (±) | 66 |
| 82 | 2-chloro-pyridin-5-yl-methyl | N-methyl-N-(4-methylpentyl)-benzyl (±) | 100 |
| 83 | 2-chloro-pyridin-5-yl-methyl | N-ethyl-N-(4-methylpentyl)-benzyl (±) | 110 |
| 84 | 2-chloro-pyridin-5-yl-methyl | 2-(2,2-dimethyl-propoxy)-pyridyl | Oil |
| 85 | 2-chloro-thiazol-5-yl-methyl | 2-(4-fluorophenoxy)-propyl (±) | 110 |
| 86 | 2-chloro-thiazol-5-yl-methyl | 2-(3,4-dimethyl-phenoxy)-propyl (±) | Oil |

USE EXAMPLES

Example A

*Phaedon larvae* test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*) for as long as the leaves are still moist.

After the desired time, the destruction in % is determined. 100% means that all the beetle larvae have been killed; 0% means that none of the beetle larvae have been killed.

In this test, a degree of destruction of 100% is shown after 7 days by the compounds according, for example, to Preparation Examples 3, 4, 5, 6, 7, 8, 9, 10, 11, 20, 21, 24, 27, 31, 32, 35, 46, 51, 52, 53, 54, 55, 56, 57, 58, 59, 60, 67, 85 and 86 at an exemplary active compound concentration of 0.1%.

Example B

Plutella test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) for as long as the leaves are still moist.

After the desired time, the destruction in % is determined. 100% means that all the beetle larvae have been killed; 0% means that none of the beetle larvae have been killed.

In this test, a degree of destruction of 100% is shown after 7 days by the compounds according, for example, to Preparation Examples 1, 4, 6, 7, 8, 10, 11, 22, 26, 27, 28, 31, 33, 45, 46, 51, 56, 59, 62, 66 and 86 at an exemplary active compound concentration of 0.1%.

Example C

Spodoptera test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Spodoptera frugiperda*) for as long as the leaves are still moist.

After the desired time, the destruction in % is determined. 100% means that all the beetle larvae have been killed; 0% means that none of the beetle larvae have been killed.

In this test, a degree of destruction of 100% is shown after 7 days by the compounds according, for example, to Preparation Examples 7, 8, 9, 10, 11, 12, 22, 23, 25, 26, 35, 37, 41, 43, 45, 46, 51, 55, 59 and 70 at an exemplary active compound concentration of 0.1%.

Example D

*Spodoptera exigua* test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Spodoptera exigna*) for as long as the leaves are still moist.

After the desired time, the destruction in % is determined. 100% means that all the beetle larvae have been killed; 0% means that hone Of the beetle larvae have been killed.

In this test, a degree of destruction of 100% is shown after 3 days by the compounds according, for example, to Preparation Examples 27, 28, 32 and 33 at an exemplary active compound concentration of 0.1%.

Example E

*Heliothis armigera* test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Soya shoots (*Glycine max*) are treated by being dipped into the preparation of active compound of the desired concentration and are infested with the cotton bollworm (*Heliothis armigera*) for as long as the leaves are still moist.

After the desired time, the destruction in % is determined. 100% means that all the caterpillars have been killed; 0% means that none of the caterpillars have been killed.

In this test, a degree of destruction of 100% is shown after 3 days by the compounds according, for example, to Preparation Examples 5, 27, 28, 32 and 33 at an exemplary active compound concentration of 0.1%.

Example F

Nephotettix test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with the rice green leafhopper (*Nephotettix cincticeps*) for as long as the seedlings are still moist.

After the desired time, the destruction in % is determined. 100% means that all the leafhoppers have been killed; 0% means that none of the leafhoppers have been killed.

In this test, a degree of destruction of 100% is shown after 6 days by the compounds according, for example, to Preparation Examples 8, 10, 11, 12, 20, 22, 23, 24, 25, 37, 41, 45, 68, 70 and 71 at an exemplary active compound concentration of 0.1%.

Example G

Myzus test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are heavily infested with the peach aphid (*Myzus persicae*) are treated by being dipped into the preparation of active compound of the desired concentration.

After the desired time, the destruction in per cent is determined. 100% means that all the aphids have been killed; 0% means that none of the aphids have been killed.

In this test, a degree of destruction of 100% is shown after 6 days by the compounds according, for example, to Preparation Examples 1, 6, 8, 9, 10, 12, 22, 25, 26, 27, 28, 29, 32, 46, 54, 59, 60 and 86 at an exemplary active compound concentration of 0.1%.

Example H

Tetranychus test (OP-resistant/dipping treatment)

Solvent: 7 parts by weight of

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water, containing emulsifier, to the desired concentration.

Bean plants (*Phaseolus vulgaris*) which are heavily infested by all stages of the common spider mite (*Tetranychus urticae*) are dipped into a preparation of active compound of the desired concentration.

After the desired time, the action in % is determined. 100% means that all the spider mites have been killed; 0% means that none of the spider mites have been killed.

In this test, a degree of destruction of 98% is shown after 13 days by the compounds according, for example, to Preparation Examples 13, 14, 15, 16 and 17 at an exemplary active compound concentration of 0.1%.

Example I

Limit concentration test/soil insects

Test insect: *Diabrotica balteata-larvae* in the soil

Solvent: 4 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added, and the concentrate is diluted with water to the desired concentration. In this context, the concentration of the active compound in the preparation is of virtually no importance, with only the quantity by weight of active compound per unit volume of soil, which is indicated in ppm (mg/l), being significant.

The soil is placed in 0.5 l pots which are left to stand at 20° C.

Immediately after mixing, 5 pregerminated maize seeds are sown in each pot. After 1 day, the test insects are placed in the treated soil. After a further 7 days, the degree of action of the active substance is determined in % by counting the dead and live test insects. The degree of action is 100% when all test insects have been destroyed, and is 0% when just as many test insects are alive as in the case of the untreated control.

In this test, a degree of destruction of 100% is shown by the compound according, for example, to Preparation Example 31 at an exemplary active compound concentration of 20 ppm.

Example J

Limit concentration test/root systemic action

Test insect: *Aphis fabae*

Solvent: 4 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added, and the concentrate is diluted with water to the desired concentration.

The preparation of active compound is intimately mixed with soil. In this context, the concentration of the active compound in the preparation is almost irrelevant, only the quantity by weight of active compound per unit volume of soil, which is indicated in ppm (=mg/l), being significant. The treated soil is placed in pots which are planted with beans (*Vicia faba*). In this way, the active compound can be taken up from the soil by the plant roots and transported into the leaves.

For detection of the root-systemic effect, the leaves only are infested with the abovementioned test organisms after 7 days. After a further 6 days, evaluation is carried out by counting or estimating the dead organisms. The root-systemic action of the active compound is derived from the destruction figures. It is 100% if all of the test organisms have been killed and 0% if just as many test insects are still alive as in the case of the untreated control.

In this test, a degree of destruction of 100% is shown by the compounds according, for example, to Preparation Examples 1, 6, 29, 31 and 32 at an exemplary active compound concentration of 20 ppm.

Example K

Blowfly larvae test/development-inhibiting action

Test organisms: *Lucilia cuprina-larvae*

Emulsifier: 35 parts by weight of ethylene glycol monomethyl ether 35 parts by weight of nonylphenol polyglycol ether To produce a suitable preparation of active compound, three parts by weight of active compound are mixed with seven parts by weight of the abovementioned mixture and the emulsifion concentrate thus obtained is diluted with water to the particular concentration desired.

About 20 *Lucilia cuprina* res. larvae are introduced into a test tube which contains about 1 cm$^3$ of horse meat and 0.5 ml of the preparation of active compound. After 24 hours and 48 hours, the activity of the preparation of active compound is determined. The test tubes are transferred into a beaker whose base is covered with sand. After a further 2 days, the test tube is removed and the pupae are counted.

The action of the preparation of active compound is assessed in accordance with the number of hatched flies after 1.5 times the development period of an untreated control. In this context, 100% means that no flies have hatched; 0% means that all of the flies have hatched normally.

In this test, destruction of 100% is shown by the compounds according, for example, to Preparation Examples 1, 3, 5, 6, 7, 10, 12, 18, 19, 20, 22, 23, 24, 25, 26, 27, 28, 31, 32, 33, 34, 35, 37, 38, 39, 40, 41, 42, 43, 44, 51, 53, 55, 56, 58, 59, 60, 61, 62, 63, 64, 65, 66, 67, 69, 70, 71 and 73 at an exemplary active compound concentration of 1000 ppm.

Example L

Test with flies (*Musca domestica*)

Test organisms: adult *Musca domestica*, Reichswald strain (OP, SP, carbamate-resistant)

Solvents: 35 parts by weight of ethylene glycol monomethyl ether 35 parts by weight of nonylphenol polyglycol ether To produce a suitable formulation, three parts by weight of active compound are mixed with seven parts of the abovementioned solvent/emulsifier mixture and the emulsifion concentrate thus obtained is diluted with water to the particular concentration desired.

2 ml of this preparation of active compound are pipetted onto filter paper dishes (Ø 9.5 cm) which are in appropriately sized Petri dishes. After drying the filter discs, 25 test organisms are transferred to the Petri dish and are covered.

After 1, 3, 5 and 25 hours, the activity of the preparation of active compound is determined. In this context, 100% means that all of the flies have been killed; 0% means that none of the flies have been killed.

In this test, destruction of 100% is shown by the compounds according, for example, to Preparation Examples 3, 6, 7, 10, 12, 18, 19, 20, 21, 22, 23, 24, 25, 26, 33, 34, 35, 37, 38, 40, 41, 42, 43, 53, 56, 59, 60, 61, 62, 63, 64, 65, 66, 67, 69, 70, 71 and 73 at an exemplary active compound concentration of 1000 ppm.

Example M

Cockroach test

Test organisms: *Periplaneta americana*

Solvents: 35 parts by weight of ethylene glycol monomethyl ether 35 parts by weight of nonylphenol polyglycol ether To produce a suitable formulation, three parts by weight of active compound are mixed with seven parts of the abovementioned solvent/emulsifier mixture and the emulsifion concentrate thus obtained is diluted with water to the particular concentration desired.

2 ml of this preparation of active compound are pipetted onto filter paper discs (Ø 9.5 cm) which are in appropriately sized Petri dishes. After drying the filter discs, 5 test organisms *P. americana* are transferred and are covered.

After 3 days, the activity of the preparation of active compound is determined. In this context, 100% means that all of the cockroaches have been killed; 0% means that none of the cockroaches have been killed.

In this test, destruction of 100% is shown by the compounds according, for example, to Preparation Examples 1, 5, 10, 23, 33, and 43 at an exemplary active compound concentration of 1000 ppm.

We claim:

1. Substituted tetrahydro-5-nitro-pyrimidines of the formula (I)

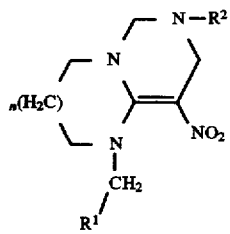

in which n represents 0 or 1, $R^1$ represents pyridyl or thiazolyl which are optionally substituted by identical or different substituents, said substituents being:

halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy and $C_1$–$C_4$-halogenoalkylthio, $R^2$ represents one of the following groups:

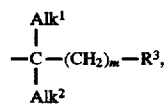 a)

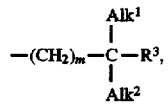 b)

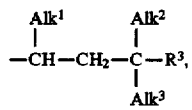 c)

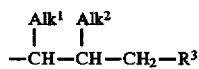 d)

-continued

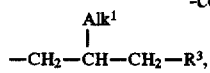 f)

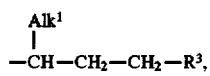 g)

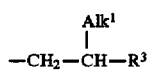 h)

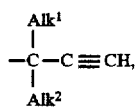 i)

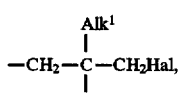 j)

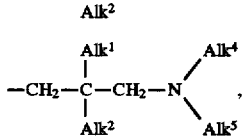 k)

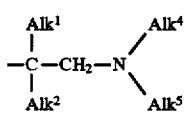 l)

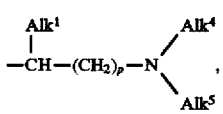 m)

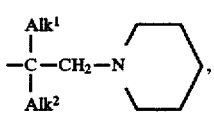 n)

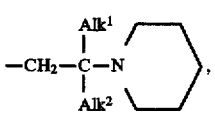 o)

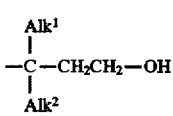 p)

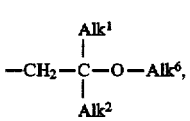 q)

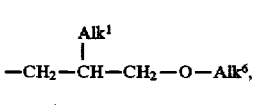 r)

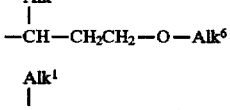 s)

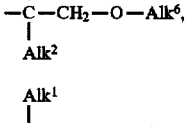 t)

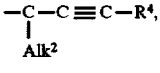 u)

-continued

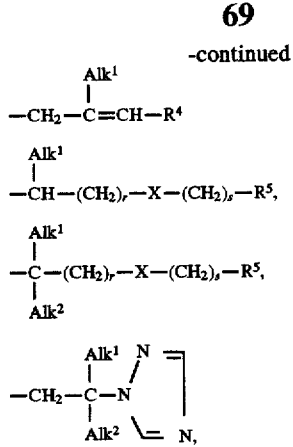

in which
  Alk represents alkyl having 1 to 4 carbon atoms,
  Alk¹ to Alk⁶ independently of one another represent alkyl having 1 to 4 carbon atoms,
  Hal represents halogen,
  m represents 1 or 2,
  p represents 1, 2 or 3,
  r and s independently of one another represent 0, 1, 2, 3 or 4,
  R³ represents phenyl or pyridyl which are optionally substituted by identical or different substituents, said substituents being:
    halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, amino, $C_1$–$C_4$-alkylamino and di($C_1$–$C_4$-alkyl)amino;
  or R³ represents N-morpholino which is optionally substituted by identical or different substituents, said substituents being:
    halogen, $C_1$–$C_4$-alkyl, $C_1$–$C_4$-alkoxy and $C_1$–$C_4$-halogenoalkyl,
  R⁴ and R⁵ independently represent phenyl or thienyl which are optionally substituted by identical or different substituents, said substituents being:
    halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, amino, $C_1$–$C_4$-alkylamino and di($C_1$–$C_4$-alkyl)amino;
  X represents oxygen, sulphur or the group NAlk⁷,
in which
  Alk⁷ represents alkyl having 1 to 4 carbon atoms.

2. Process for the preparation of substituted tetrahydro-5-nitro-pyrimidines of the formula (I) according to claim 1

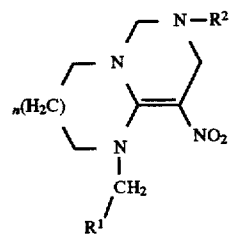

in which
  n represents 0 or 1,
  R¹ represents pyridyl or thiazolyl which are optionally substituted by identical or different substituents, said substituents being:
    halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy and $C_1$–$C_4$-halogenoalkylthio, R² represents one of the following groups:

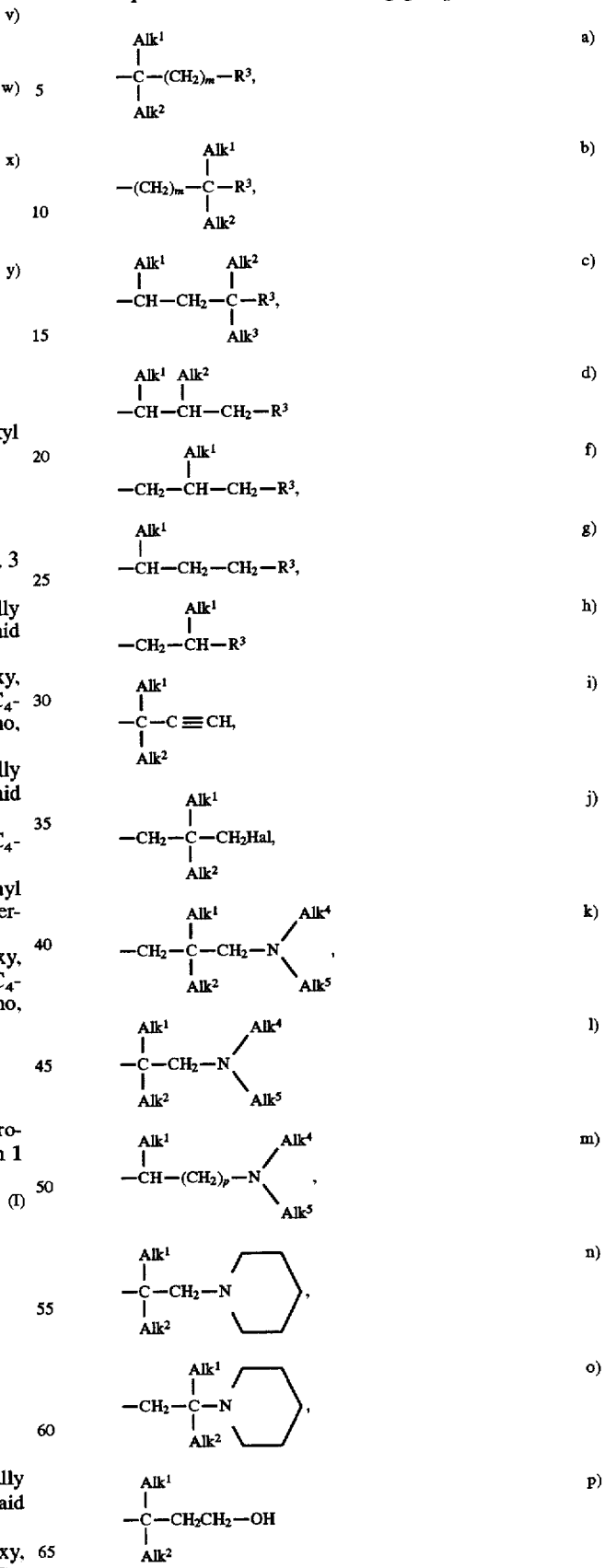

-continued

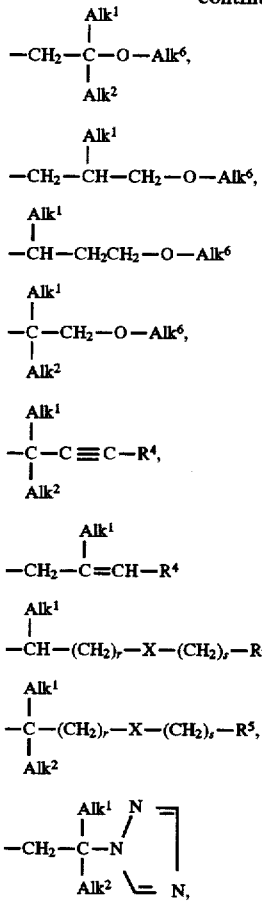

in which
Alk represents alkyl having 1 to 4 carbon atoms,
Alk$^1$ to Alk$^6$ independently of one another represent alkyl having 1 to 4 carbon atoms,
Hal represents halogen,
m represents 1 or 2,
p represents 1, 2 or 3,
r and s independently of one another represents 0, 1, 2, 3 or 4,
R$^3$ represents phenyl or pyridyl which are optionally substituted by identical or different substituents, said substituents being:
halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, amino, $C_1$–$C_4$-alkylamino and di($C_1$–$C_4$-alkyl)amino;
or R$^3$ represents N-morpholino which is optionally substituted by identical or different substituents, said substituents being: halogen, $C_1$–$C_4$-alkyl, $C_1$–$C_4$-alkoxy and $C_1$–$C_4$-halogenoalkyl, R$^4$ and R$^5$ independently represent phenyl or thienyl which are optionally substituted by identical or different substituents, said substituents being:
halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio, amino, $C_1$–$C_4$-alkylamino and di($C_1$–$C_4$-alkyl)amino;
X represents oxygen, sulphur or the group NAlk$^7$,
in which
Alk$^7$ represents alkyl having 1 to 4 carbon atoms;
wherein nitromethylene derivatives of the formula (II)

$$\text{(II)}$$

in which
R$^1$ and n have the meaning given above
are reacted with amines of the formula (III)

$$H_2N-R^2$$

in which
R$^2$ has the meaning given above
in the presence of at least twice the molar quantity of formaldehyde, optionally in the presence of an acidic catalyst and optionally in the presence of a diluent.

3. Composition for combating pests comprising a pesticidally effective amount of at least one tetrahydro-5-nitro-pyrimidine of the formula (I), according to claim 1.

4. Method of combatting pests comprising causing a tetrahydro-5-nitro-pyrimidine of the formula (I), according to claim 1, to act on pests and/or their habitat.

5. Process for the production of compositions for combating pests comprising mixing a tetrahydro-5-nitro-pyrimidine of the formula (I), according to claim 1, with extenders and/or surface-active agents.

6. A composition for combatting pests, according to claim 3, which further includes extenders and/or surface-active agents.

7. A method of combatting pests according to claim 4, wherein the tetrahydro-5-nitro-pyrimidine further includes extenders and/or surface-active agents.

8. The product of the process of claim 5.

* * * * *